(12) United States Patent
Ljungmann et al.

(10) Patent No.: US 7,754,147 B2
(45) Date of Patent: Jul. 13, 2010

(54) STAINING MACHINE FOR TREATMENT OF TISSUE SPECIMENS

(75) Inventors: Oystein Ljungmann, Siggerud (NO); Torstein Ljungmann, Oslo (NO)

(73) Assignee: Dako Instrumec AS, Oslo (NO)

( * ) Notice: Subject to any disclaimer, the term of this patent is extended or adjusted under 35 U.S.C. 154(b) by 1231 days.

(21) Appl. No.: 10/537,826

(22) PCT Filed: Dec. 17, 2002

(86) PCT No.: PCT/NO02/00484

§ 371 (c)(1),
(2), (4) Date: Oct. 28, 2005

(87) PCT Pub. No.: WO2004/055497

PCT Pub. Date: Jul. 1, 2004

(65) Prior Publication Data

US 2006/0127276 A1 Jun. 15, 2006

(51) Int. Cl.
G01N 21/13 (2006.01)
(52) U.S. Cl. .......................... 422/65; 422/130; 436/47; 436/48
(58) Field of Classification Search .................. 422/65, 422/130; 436/47, 48; 118/425, 423
See application file for complete search history.

(56) References Cited

U.S. PATENT DOCUMENTS 4,738,824 A   4/1988   Takeuchi
4,911,098 A * 3/1990   Tabata ..................... 118/423
5,601,650 A   2/1997   Goldbecker et al.
6,436,348 B1 * 8/2002  Ljungmann et al. .......... 422/63
2001/0019703 A1 9/2001 Thiem et al.

FOREIGN PATENT DOCUMENTS

JP         4-279838       10/1992

* cited by examiner

Primary Examiner—Jill Warden
Assistant Examiner—Natalia Levkovich
(74) Attorney, Agent, or Firm—Buchanan Ingersoll & Rooney PC

(57) ABSTRACT

A Staining machine for treatment of tissue specimens on slides placed in baskets (9) includes a number of baths (7, 12) placed successively in a row (6 resp. 11), and a device for successive transport of the baskets in a transport path from one bath to the next one, the baskets (9) being transported from an input station (5) to an output station (14) in accordance with a predetermined treatment program. The machine includes at least two bath rows (6 resp. 11) placed juxtaposed and parallel with each other, the first bath row (6) extending from the input station (5) to an opposite end of this row, and second path row (11) extending from the output station (14) to an opposite end of this row. Further, the machine includes a first device (8, 21, 22) for transport of baskets (9) in a first transport path from the input station (5) to the opposite end of the first row (6), a second device (13, 15-19) for transport of baskets (9) in a second transport path towards the output station (14) from the opposite end of the second row (11), and a device for transfer of baskets between the transport paths of opposite ends of the rows belonging together.

4 Claims, 4 Drawing Sheets

STAINING MACHINE FOR TREATMENT OF TISSUE SPECIMENS

The invention relates to a staining machine for treatment of tissue specimens on slides placed in baskets, which machine includes a number of baths placed successively in a row, and a device for successive transport of the baskets in a transport path from one bath to the next one, the baskets being transported from an input station to an output station in accordance with a predetermined treatment program.

Linear staining machines (stainers) of the above-mentioned type are previously known in different embodiments. Such staining machines are used for the staining of tissue specimens by dipping into a number of chemical baths, for thereafter by microscoping to visualize tissue cells and possible cell changes for diagnosing and is possible treatment. These tissue specimens are placed on slides which in turn are placed in a certain number in a basket which is equipped with a suspension to be able to be transported from one chemical bath to the next one.

Linear stainers are used in cytological laboratories which usually run only one routine program, but which have a need for a high capacity, in contradistinction to histological laboratories which use several staining programs, but which as a rule have a somewhat smaller capacity demand and will be better served with a flexible programmed robot staining machine. Linear stainers distinguish themselves in that they lift all the present baskets simultaneously from one both to the next one, and with an equal dipping time in all baths which are placed successively in one row. The dipping time normally is from one to two minutes in each bath. In order to be able to have a similar dipping time in each bath, the chemicals in some cases must be diluted, and for other chemicals one has the same reagent in several baths after one another in order to achieve a sufficient long dipping time. The necessary number of baths for the most common staining programs therefore will be around 20 to 25 baths.

This means that the known linear staining machines with input and output stations and with all baths placed successively in one row, requires a length of 1,5 to 2 meters of the laboratory bench, dependent on the number of baths and the size thereof. This is a substantial drawback in laboratories which are often characterised by lack of space.

The object of the invention therefore is to provide a staining machine which is constructed such that the building length is substantially reduced.

This object is achieved with a staining machine of the introductorily stated type which, according to the invention, is characterised in that the machine includes at least two bath rows placed juxtaposed and parallel with each other, the first path row extending from the input station to an opposite end of the row, and a second bath row extending from the output station to an opposite end of the row, a first device for transport of baskets in a first transport path from the input station to the opposite end of the first row, a second device for transport of baskets in a second transport path towards the output station from the opposite end of the second row, and a device for the transfer of baskets between the transport paths at opposite ends belonging together of the relevant rows.

An advantageous embodiment of the staining machine according to the invention is characterised in that it includes only a first and a second bath row, the input and output stations being situated next to each other, and the device for transfer of baskets being a crossbar device which is arranged to transfer baskets between two baths that are situated next to each other at said opposite ends of the two rows.

With this construction the above-mentioned space problems are substantially reduced in that the machine is constructed with two parallel transport paths wherein one path brings the baskets in one row from the input station to an end position where the baskets one by one by means of a crossbar device is transferred to the other transport path where the baskets are transported in one row back to the output station. This means that one half of the baths as well as the input and output stations stand side by side and thus require only half of the building length. One could also imagine several parallel paths, but in the present case one has chosen only two paths in order to have a construction which is as simple as possible.

The invention will be further described below in connection with an exemplary embodiment with reference to the drawings, wherein FIG. 1 shows a perspective view of a staining machine according to the invention, with bonnets mounted thereon;

Figure 1:
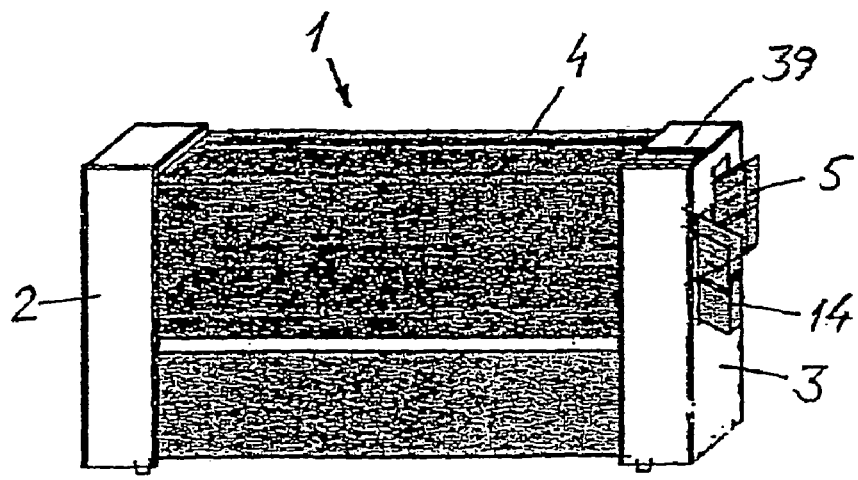
Figure 2:
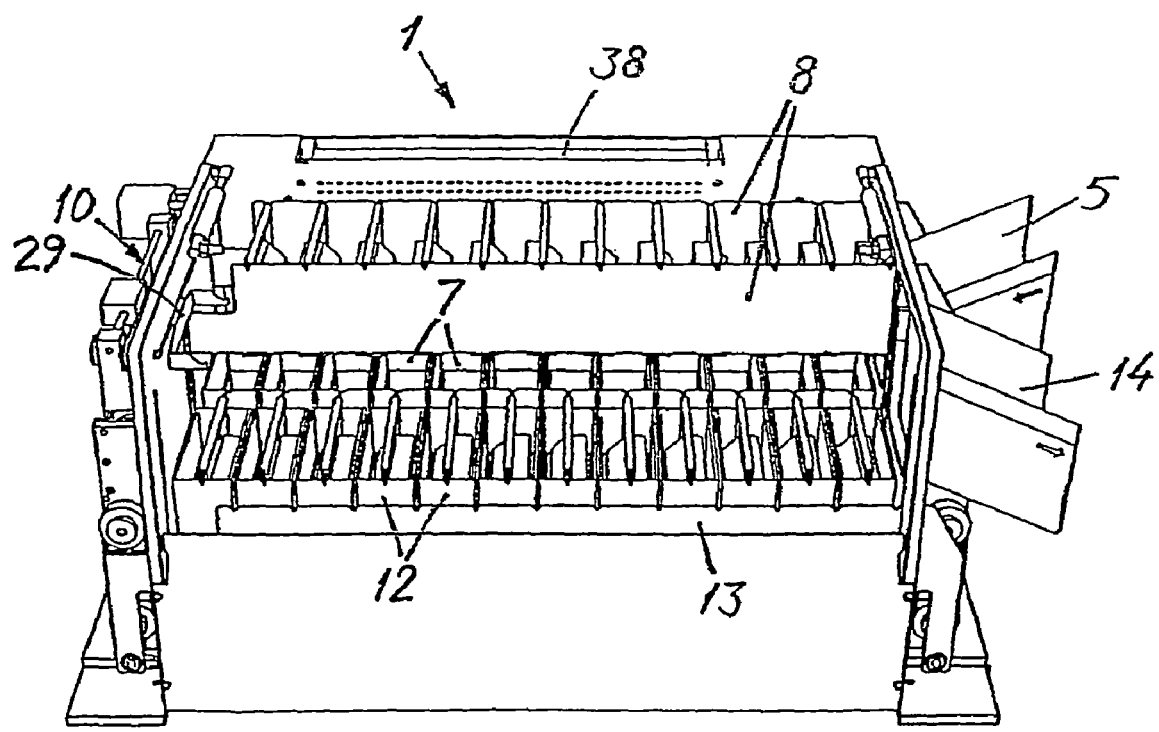
FIG. 2 shows a perspective view of the staining machine in FIG. 1, viewed from the side and aslant from above, but with the bonnets removed.

In FIG. 1 an embodiment of the staining machine 1 according to the invention is shown with end bonnets 2 and 3 and a top bonnet 4 mounted thereon. FIG. 2 shows the same machine with the bonnets removed.

As appears from FIG. 2 and FIGS. 3-5, the machine 1 includes an input station 5, an input row or entry row 6 consisting of twelve baths 7 (baths Nos. 1-12 reckoned in the direction from the input station), a first transport device 8 for lifting and transport of baskets 9 in the input row 6, a crossbar device 10 for transfer of baskets, an output row or exit row 11 consisting of twelve baths 12 (baths Nos. 13-24 reckoned in the direction towards the output station), a second transport device 13 for lifting and transport of baskets in the output row 11, and an output station 14.

Both the input station 5 and the output station 13 are presupposed to have a space for four or more baskets. The first transport device 8 fetches baskets 9 from the input station 5 and moves one or more baskets from one bath to the next one in the input row 6. The crossbar device 10 is arranged to transfer one basket 9 at a time after lifting-out of the basket from the last bath in the row (bath No. 12) over to the output row 11 where the second transport device 13 lifts off the basket and lowers this into the first bath in the output row (bath No. 13), and subsequently transports baskets successively from said bath towards the output station 14.

Figure 4:
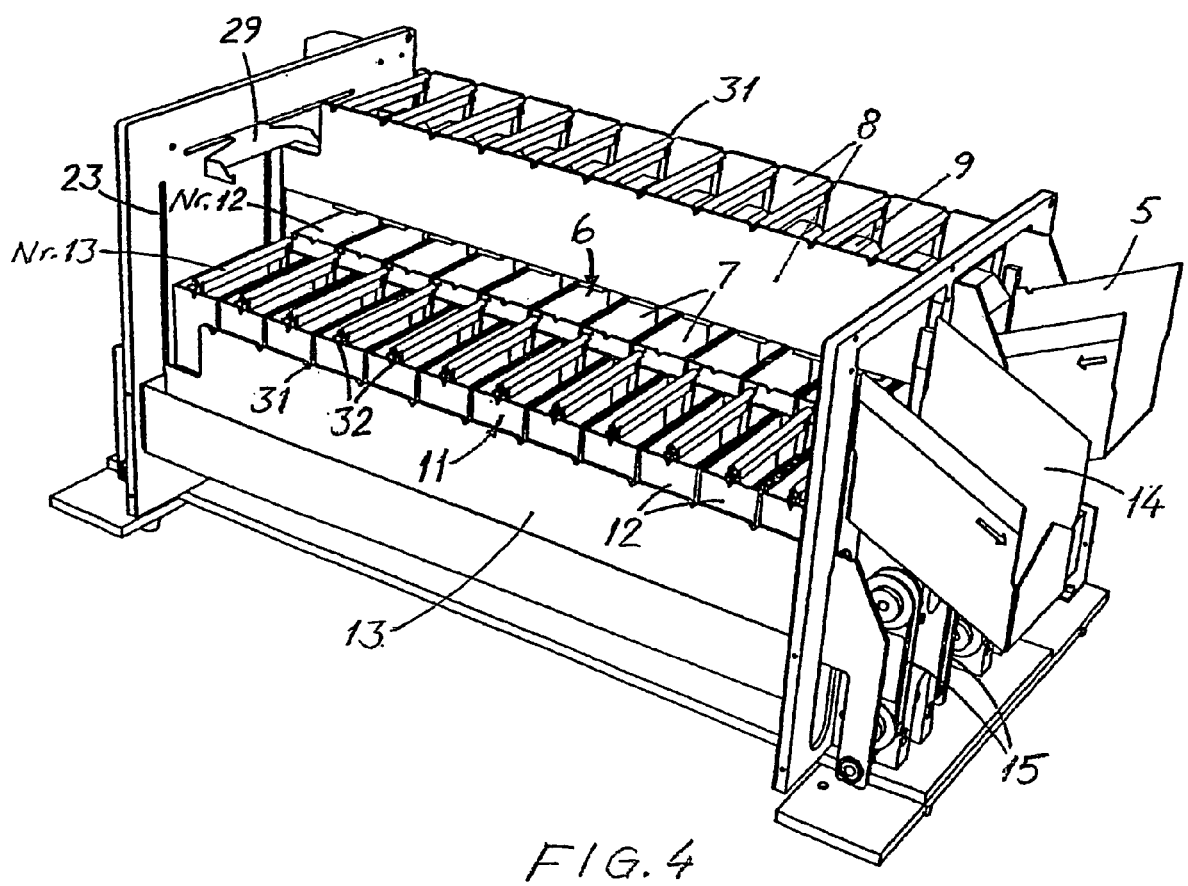
FIG. 4 shows a perspective view of the machine, viewed aslant from above in the direction towards the input/output end.
Figure 5:
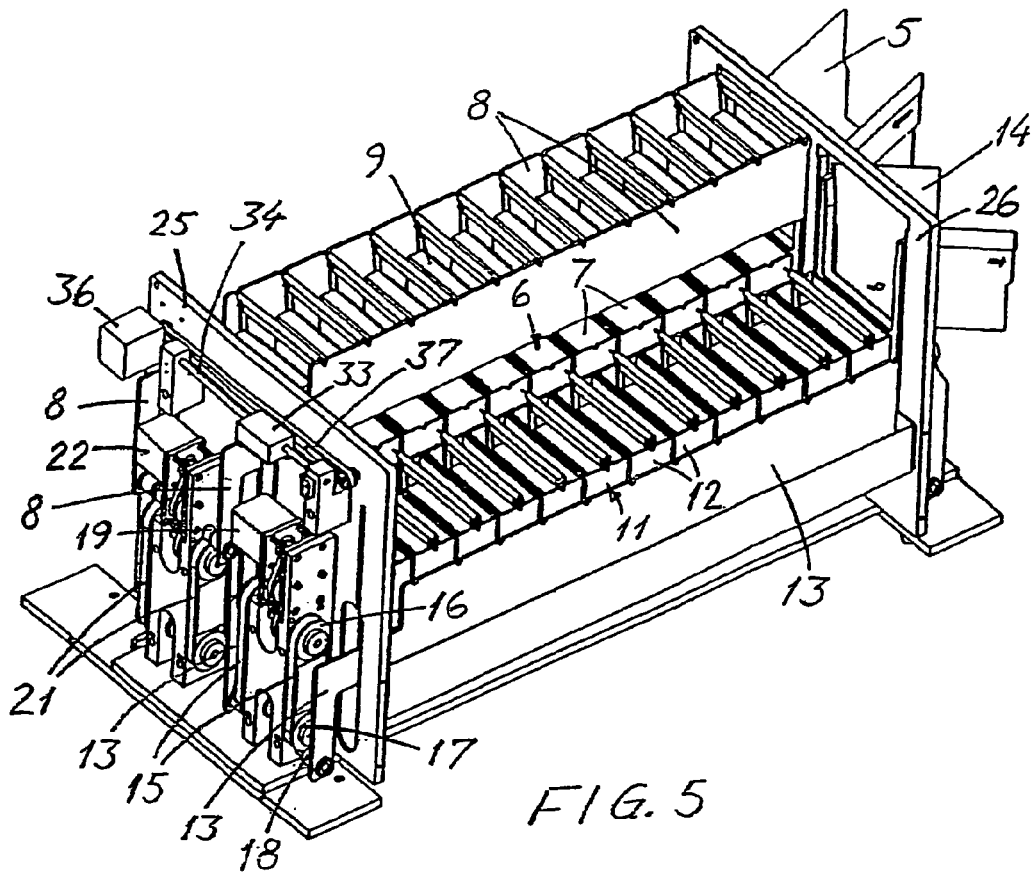
FIG. 5 shows a perspective view of the machine, viewed aslant from above and in the direction towards the opposite end in relation to FIG. 4.

As best shown in FIG. 5, each of the first and second transport devices comprises a cooperating pair of lifting/transport strings or cheeks 8 and 13, respectively. In FIGS. 2, 4 and 5 the lifting/transport cheeks 8 for the input row 6 are shown in an upper lifting position, whereas the lifting/transport cheeks 13 for the output row 11 are shown in a lower position.

Figure 6:
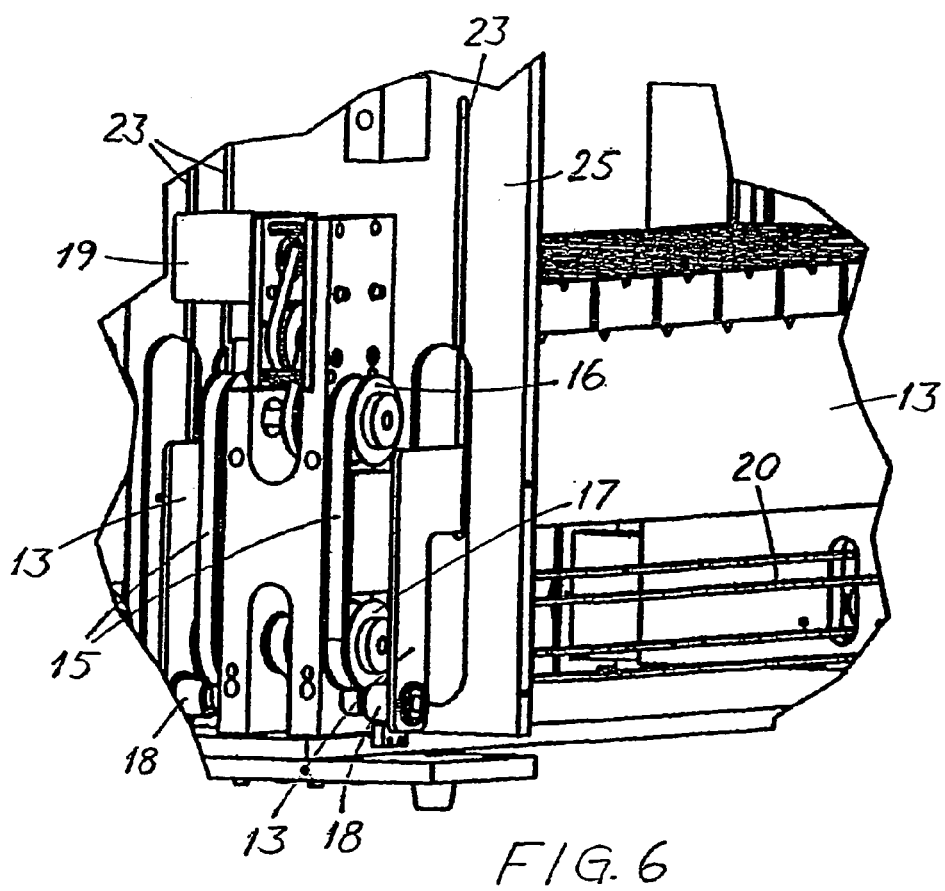
FIG. 6 shows a segment of a part of the mechanism for movement of one of the transport devices of the machine, on an enlarged scale.

The intended lifting and transport movement of each cheek pair is achieved by means of cooperating pairs of toothed belts with carriers running over appurtenant pairs of upper and lower guide wheels and consequently lifting the cheek pair in question in a stadium-shaped movement. Thus, FIG. 5 and 6 show that, at one end of the machine there is arranged a first pair of toothed belts 15 of which each runs over an upper and a lower guide wheel 16 and 17, respectively, the adjacent ends of the lifting/transport cheeks 13 for the output row 11 being coupled to an appurtenant toothed belt via a respective carrier 18. The toothed belts 15 are driven by a step motor 19 via a toothed belt gear.

Figure 3:
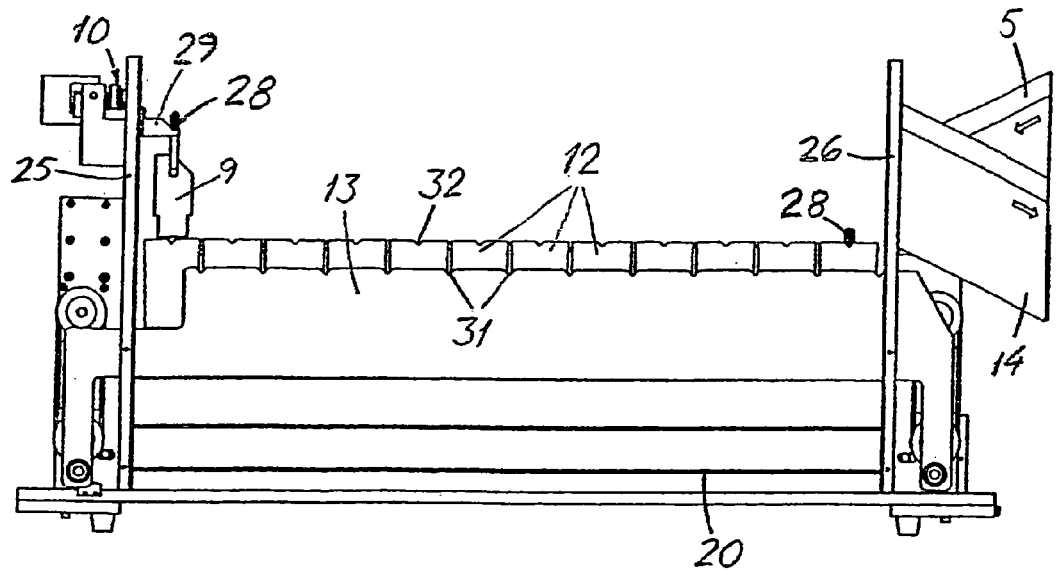
FIG. 3 shows a side view of the machine.

A corresponding pair of toothed belts 15 and guide wheels 16, 17 is arranged at the other end of the machine, as appears from FIGS. 3 and 4. The toothed belt pairs at each end of the machine work synchronously by means of an additional toothed belt 20 which transfers the movement of the driven toothed belts to the toothed belts at the other end of the machine.

A drive arrangement corresponding to that described above in connection with the lifting/transport cheeks 13 for the output row 11, is arranged for the lifting/transport cheeks 8 for the input row 6, as appears from FIG. 5. In this Figure, the illustrated pair of toothed belts for this cheek pair is designated by 21, and the drive motor for these is designated by 22.

Both pairs 8 and 13 of lifting/transport cheeks are laterally guided in respective vertical slots 23 and 24 arranged in two wall elements 25 and 26 forming transversely extending end walls at the ends of the bath rows.

Figure 7:
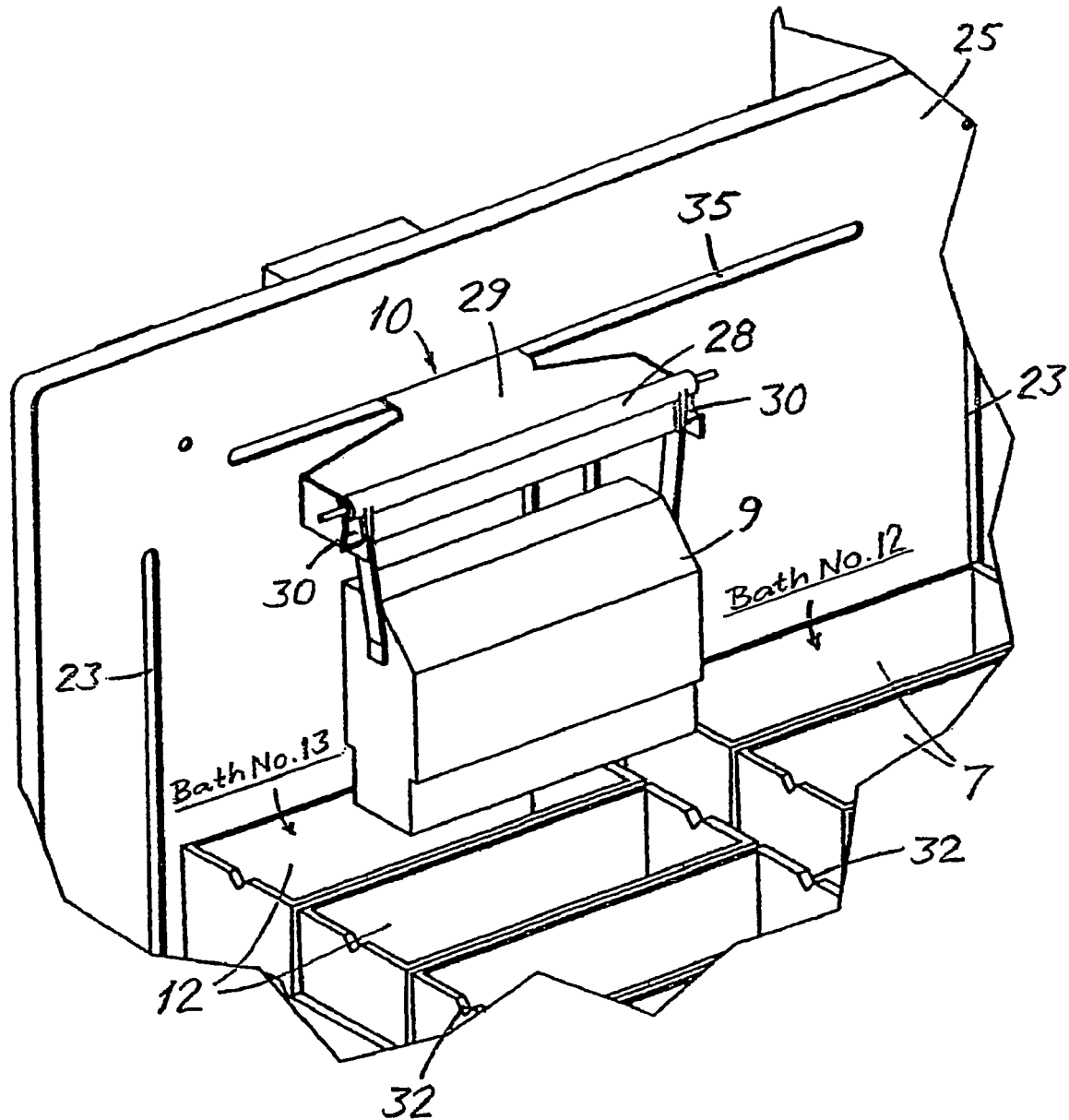
FIG. 7 is an enlarged detail segment showing the crossbar device and a basket suspended therefrom.

As appears from FIGS. 3 and 7, the baskets 9 (which contain non-illustrated slides) are provided with a suspension 28 which is adapted to be hung off on a traverse or crossbar bracket 29 during the transverse or lateral transfer of the baskets from the input row to the output row. The suspensions 28 comprise a rod which, at each end, is provided with a lifting hook 30 which is adapted to engage in corresponding notches 31 in an upper side edge of the lifting/transporting cheeks 8 and 13, when the baskets are lifted up from the baths 7 and 11. Each of the baths is also provided with notches 32 belonging together in upper side edges thereof, for receiving the suspension hooks 30 when the baskets are lowered into the baths.

As appears from FIG. 5, the crossbar device 10 comprises a slide block 33 sliding on a horizontal guide rod 34, and to which the crossbar brackets 39 is fastened via a slot 35 in the end wall 25. The slide block is driven back and forth by means of a step motor 36 via a toothed belt 37.

In addition to the components described above, the staining machine according to the invention also includes some additional devices which are not further shown, but which will be described briefly below. Among other things, the machine includes a freshwater connection which, via an electrically operated water valve and a manifold with manual cocks, supplies up to four baths with water flowing over and flushing the specimens and flowing out via a bottom chest to an outlet. A microprocessor controls the water valve and the different step motors driving the movable components of the machine. A microswitch which is activated during loading, registers that a basket is loaded in and that the latest loaded basket is to be transported through 24 baths to an output station before the machine is stopped automatically. A microswitch which is activated during the unloading, registers that a basket is unloaded and delivers an acoustic signal. The machine is also equipped with a ventilation system having a filter absorbing vapour from solvents used in the baths. This filter is suggested at 38 in FIG. 2.

Further, the machine is equipped with a display (suggested at 39 in FIG. 1) for programming and error warning, and with a set of switches for Start, Stop, Menu and Reset, and with Up/Down buttons for scrolling in the menu and change of parameter values.

In operation of the machine, the lifting/transport cheeks move—as mentioned above—in a stadium-shaped movement and in this way lift the baskets vertically up from the baths, and further in a semi-circular movement over to the next bath and vertically into this. The suspensions 28 then become hanging in the notches 32 in the upper edge of the baths, whereas the lifting/transport cheeks which are then released, can carry out an additional semi-circular movement back to a new fetching position. The lifting/transport cheeks also provide for delivering baskets 9 from the end bath, i.e. bath No. 12 in the input row, to the crossbar bracket 29 which transfers the baskets from the input row to the output row where the lifting/transport cheeks lift the baskets from the crossbar bracket and down into the first bath, i.e. bath No. 13, in the output row.

A complete working cycle in operation of the machine will be described below.

The home position of the two pairs of lifting/transport cheeks is in the lowermost position (microswitches deliver signals in this position). The home position of the crossbar bracket is above the input row. After manual feeding of one or more baskets into the input station, the starting switch is depressed to start the process. The lifting/transport cheeks for the output row move clockwise to a vertical upward movement in order to lift out a possible basket in bath No. 13 to bath No. 14 to thereby release bath 13. The crossbar bracket moves to a position above the output row in order not to stand in the way for the lifting/transport cheeks for the input row which also move clockwise and lift up a basket present in bath No. 12 to the highest point midway between bath 12 and bath 11. The crossbar bracket returns to the input row above bath 12, and the lifting/transport cheeks for the input row rotate back and put away the basket coming from bath 12 in the crossbar bracket which transports this laterally to directly above bath 13. The lifting/transport cheeks for the output row go from the lower position and clockwise upwards and lift out the basket from the crossbar bracket and stop in the upper position with the basket situated midway between the baths 13 and 14. (At the same time all the remaining baskets in the output row are lifted out from their baths and carried halfway to the next one). The crossbar bracket returns to the input row above bath 12, and the lifting/transport cheeks for the output row return down again and put the basket from the crossbar bracket into bath 13 and the remaining baskets back into the baths from which they came. The crossbar bracket moves to a position above the output row in order not to stand in the way for the lifting/transport cheeks for the input row which now carry out a complete stadium movement anti-clockwise, so that a possible basket in the input station is fetched out and into bath 1, and the remaining present baskets are lifted one bath further, and the crossbar bracket returns to the input row above bath 12.

After a programmed "bathing time" the process is repeated in that all baskets in the output row are transported one position further, so that bath 13 is released for a new crossbar transport of a basket from bath 12.

The invention claimed is:

1. A staining machine for treatment of tissue specimens on slides placed in baskets, which machine includes:
   a number of baths placed successively in two juxtaposed and parallel bath rows, the first bath row extending from an input station located at a first end of the staining machine to an opposite end of the first bath row located at a second end of the staining machine, and the second bath row extending from an output station located at the first end of the staining machine to an opposite end of the second bath row located at the second end of the staining machine;

a first transport device for successive and simultaneous transport of the baskets in the first bath row from one bath to the next one from the input station to the opposite end of the first bath row, a second transport device for successive and simultaneous transport of the baskets in the second bath row from one bath to the next one from the opposite end of the second bath row to the output station, a device for the transfer of baskets from a bath at the opposite end of the first bath row to a bath at the opposite end of the second bath row;

wherein each of said first and second transport device comprises a pair of cheeks extending along respective sides of the first and second bath rows and being adapted for engagement with respective baskets, and wherein the staining machine further comprises a device for lifting and lowering of each of the cheek pairs for successive movement of baskets from bath to bath;

wherein the lifting and lowering device comprises a pair of toothed belts of which each runs in a closed path over an upper and a lower guide wheel comprised in the staining machine, and of which each is coupled to an end portion of a respective cheek via a carrier, and wherein the staining machine further comprises a step motor by means of which the toothed belts are driven synchronously;

wherein the pair of toothed belts at an end of the machine are coupled via an additional toothed belt to a corresponding pair of toothed belts arranged at an opposite end of the machine with appurtenant guide wheels and carriers at the other end of the cheeks, so that the cheeks are lifted and lowered synchronously at each end thereof; and wherein the baskets are transported from the input station to the output station in accordance with a predetermined treatment program.

2. A staining machine according to claim 1, wherein the input and output stations are situated next to each other, and the device for the transfer of baskets comprises a crossbar device.

3. A staining machine according to claim 2, wherein the crossbar device comprises a crossbar bracket which is adapted for releasable connection with a basket, and which is coupled to a means for reciprocating movement of the crossbar bracket in a horizontal path.

4. A staining machine according to claim 3, further comprising movement means comprising a slide block which is coupled to the crossbar bracket and is displaceable on a horizontal guide rod, the slide block being coupled to a toothed belt which is driven back and forth by means of a step motor.

* * * * *